United States Patent [19]

Kohama et al.

[11] Patent Number: 5,443,972
[45] Date of Patent: Aug. 22, 1995

[54] PROCESS TO PREPARE LEUSTRODUCSINS

[75] Inventors: Takafumi Kohama; Isao Kaneko; Takemichi Nakamura, all of Tokyo; Takeshi Kagasaki, Iwaki; Ryuzo Enokita, Tsukuba; Keiichi Matsuda, Tokyo, all of Japan

[73] Assignee: Sankyo Company, Limited, Tokyo, Japan

[21] Appl. No.: 239,284

[22] Filed: May 6, 1994

Related U.S. Application Data

[62] Division of Ser. No. 857,162, Mar. 25, 1992, Pat. No. 5,334,587.

[30] Foreign Application Priority Data

Mar. 27, 1991 [JP] Japan ................................ 3-63087

[51] Int. Cl.[6] .......................................... C12P 17/06
[52] U.S. Cl. .................................... 435/125; 435/903
[58] Field of Search ............................ 435/125, 903

[56] References Cited

U.S. PATENT DOCUMENTS

| | | | |
|---|---|---|---|
| 3,592,925 | 7/1971 | Evans et al. | 435/903 |
| 3,907,779 | 9/1975 | DeBoer et al. | 435/903 |
| 4,575,500 | 3/1986 | Burg et al. | 435/128 |
| 5,021,406 | 6/1991 | Maeda et al. | 514/99 |
| 5,334,587 | 8/1994 | Kohama et al. | 514/99 |

FOREIGN PATENT DOCUMENTS

| | | | |
|---|---|---|---|
| 0139458 | 5/1985 | European Pat. Off. | 435/125 |
| 0329361 | 2/1989 | European Pat. Off. | |
| 2-186 | 4/1988 | Japan | |

OTHER PUBLICATIONS

*Br. J. Cancer* (1989), 59, "Clinical Significance of the Haemopoietic Growth Factors"; S. Devereux et al; pp. 2–5.

*Nippon Acta Radiologica*, (1988), 48, (4), "Restorative Effect of MDP-Lys (L18) on Leukopenia of Cancer Patient Treated With Radiotherapy"; T. Okawa et al; pp. 514–522.

*Exp. Hematol.*, (1988), 16, "A Burst–promoting Activity Derived from the Human Bone Marrow Stromal Cell Line KM-102 Is Identical to the Granulocyte–Macrophage Colony–Stimulating Factor", T. Kohama et al; pp. 603–608.

*Science*, (1984), 225, "Turnover of Inositol Phospholipids and Signal Transduction"; Y. Nishizuka; pp. 1365–1370.

*J. Cell Physiol.*, (1977), 91, "Conditions Controlling the Proliferation of Haemopoietic Stem Cells in Vitro", T. M. Dexter et al; pp. 335–344.

*Proc. Natl. Acad. Sci. USA*, (1985), 82, "Generation of Functional Clonal Cell Lines From Human Bone Marrow Stroma", K. Harigaya et al; pp. 3477–3480.

*The Journal of Antibiotics*, (1989), XLII, "Novel Antitumor Antibiotic Phospholine"; T. Ozasa et al; pp. 1331–1338.

*Primary Examiner*—Herbert J. Lilling
*Attorney, Agent, or Firm*—Frishauf, Holtz, Goodman & Woodward

[57] ABSTRACT

New compounds, which we have named the "Leustroducsins" have the formula (I):

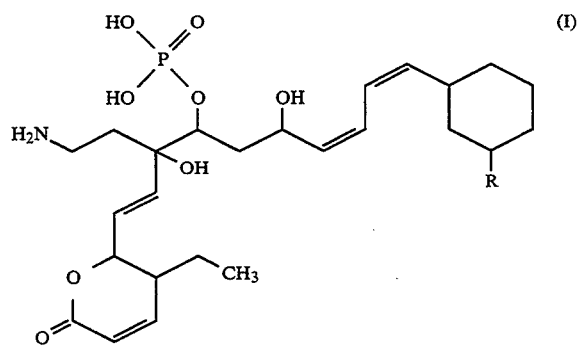

in which R represents a 5-methylhexanoyloxy group, a 6-methyloctanoyloxy group or a 7-methyloctanoyloxy group, and salts thereof, and may be prepared by fermentation using a microorganism of the genus *Streptomyces*, especially a strain of the species *Streptomyces platensis*, such as strain SANK 60191 (FERM BP-3288). These compounds may be used for the treatment or prophylaxis of: adverse reactions resulting from cancer chemotherapy or radiotherapy; infections; cancer; cerebral dysfunction; and fungal infections.

10 Claims, No Drawings

PROCESS TO PREPARE LEUSTRODUCSINS

This is a division of application Ser. No. 07/857,162, filed Mar. 25, 1992, now U.S. Pat. No. 5,334,587, issued Aug. 2, 1994.

BACKGROUND OF THE INVENTION

The present invention provides a series of new compounds which we have named "Leustroducsin A", "Leustroducsin B" and "Leustroducsin C". These compounds have the formula (I), shown hereafter. The invention also provides methods of preparing these compounds by fermentation using a microorganism of the genus *Streptomyces*, and especially a strain of the species *Streptomyces platensis*, which is also new and also forms part of the present invention. The compounds of the invention have a variety of therapeutic effects, and, thus, the invention also provides compositions and methods of therapy or prophylaxis using these compounds.

The leustroducsins of the present invention are novel compounds which stimulate the production of hematopoietic factors, such as granulocyte colony-stimulating factor (hereinafter abbreviated to "G-CSF") and granulocyte-macrophage colony-stimulating factor (hereinafter abbreviated to "GM-CSF"); they also stimulate the production of nerve growth factor (hereinafter abbreviated to "NGF"); moreover, they exhibit an antifungal effect, e.g. against *Tricophyton mentagrophytes*.

Various kinds of cytokines having a hematopoiesic activity, such as colony-stimulating factors (hereinafter abbreviated to "CSF"), and several kinds of glycoproteins (generally named the "interleukins") have to date been prepared by the techniques of gene manipulation. These substances have been used clinically in various ways to reduce the adverse side effects commonly caused by cancer chemotherapy and radiotherapy and to block infection. The effectiveness of these substances has recently become clear [Br. J. Cancer 59, 2–5 (1989)].

It has been found that the administration of these factors themselves to humans by various routes results in clear pharmacological effects, which leads to the possible use of these factors in therapy. However, it is thought that these factors are essentially produced in vivo by certain kinds of cells (e.g. lymphocytes, monocytes, fibroblasts, vascular endothelial cells and stromal cells) through a complicated regulatory system, and that they play homeostatic roles in the production of various kinds of blood cells. Accordingly, if these factors are administered without any consideration for the delicate balance of this regulatory mechanism, several side effects may be observed, which may be caused by the imbalance of this regulatory mechanism; examples of such side effects include inflammation at the site of injection, bone pain, fever and rigor.

On the other hand, instead of administering the hematopoietic factors themselves, it might be possible to administer certain substances which are known to stimulate the production of these hematopoietic factors in the body. For example, it is known that interleukin 1 (hereinafter abbreviated to IL-1) and tumor necrosis factor (hereinafter abbreviated to TNF) can induce the production of CSF etc. by various kinds of cells. These factors, however, cannot always act as specific inducers of hematopoietic factors because they also have various other biological activities.

It is also known that various kinds of low-molecular weight immunoactivators, such as lipopolysaccharides (hereinafter abbreviated to LPS) and muramyldipeptides (hereinafter abbreviated to LDP) can produce various kinds of CSF's by activation of monocytes and macrophages. However, it is known that other physiological effects caused by the activation of macrophages, for example the production of monokines such as IL-1 and TNF occurs at the same time, which can result in various side effects, such as fever [Nippon Acta Radiologica 48, (4), 514 (1988)].

Phorbol esters and calcium ionophores are known to induce CSF production synergistically [Kohama et al.: Experimental Hematology 16, 603–608 (1988)], however, they are also known not only to stimulate the production of hematopoietic factors but also to stimulate the production and secretion of the whole of the secreting proteins, including hormones such as insulin [Y. Nishizuka: Science 225, 1365 (1984)].

Although the precise mechanism has not yet been clarified, it is thought that, in the formation of blood cells, various kinds of mature blood cells can be formed from common cell precursors, called hematopoietic stem cells, through the action of various hematopoietic factors and through cell to cell interaction. It has been established that the site where blood cells are formed in normal adults is limited only to the inside of the bone marrow, that cells called stromal cells existing in the bone marrow play an important role in formation of blood cells [Dexter et al.: J. Cell. Physiol. 91, 335 (1977)], and that stromal cells in the bone marrow produce various hematopoietic factors [Harigaya et al.: Proc. Natl. Acad. Sci. USA 82, 3477 (1985); Kohama et al.: Experimental Hematology 16, 603–608 (1988)].

Therefore, if a substance which stimulates the production of hematopoietic factors by stromal cells can be found, this substance may not only play a very important role in analyzing the action of the hematopoietic mechanism in physiological conditions and in the pathology of hematologic diseases but it may also find considerable clinical use.

European Patent Publication No. 329 361 discloses certain new 2-pyranone derivatives which resemble the compounds of the present invention except that they differ in the nature of the group "R", defined hereafter. Those prior art compounds are also only said to be agricultural biocides and are not shown in the published art to have the valuable and unexpected therapeutic and prophylactic activities of the compounds of the present invention. Although the prior art compounds are produced, like the compounds of the present invention, by a microorganism of the species *Strepomyces platensis*, the strain described in the prior document is believed to be clearly different from that described herein.

Very similar compounds and microorganisms, having essentially the same disclosed utility, are described in Japanese Patent Application Kokai Hei 2-186, and these are likewise thought to be clearly distinct from the compounds and microorganism disclosed herein. The Journal of Antibiotics, Vol. XLII, No. 9, page 331 discloses a novel antitumor compound, which the authors call "Phospholine", and which is produced by a microorganism of the genus *Streptomycet*, which was then newly isolated. However, the microorganism is clearly said to be *Streptomyces hygroscopicus* and is distinguished from the *Streptomyces platensis*, which is used in the present invention. Moreover, although the prior art phospholine, like the compounds of the present invention, has both an amino group and a phosphoric group, it has a different molecular formula is thus clearly distinguished.

BRIEF SUMMARY OF INVENTION

It is, therefore, an object of the present invention to provide a series of new phosphoric acid compounds having a variety of pharmacological activities.

In particular, it is believed that the compounds of the present invention have the following activities: they reduce adverse reactions resulting from cancer chemotherapy or radiotherapy; they protect against infections; they activate macrophages and thus have an anticancer effect; they improve cerebral function; and, in addition, they act as antifungal agents.

Thus, the present invention provides compounds of formula (I):

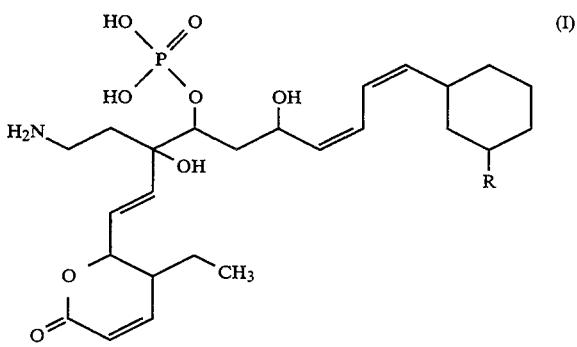

(I)

in which R represents a 5-methylhexanoyloxy group, a 6-methyloctanoyloxy group or a 7-methyloctanoyloxy group, and salts thereof. These compounds have been named by us "Leustroducsin A", "Leustroducsin B" and "Leustroducsin C", respectively.

The invention also provides a process for preparing the leustroducsins, which comprises cultivating a leustroducsin-producing microorganism of the genus *Streptomyces* and collecting at least one leustroducsin from the culture.

The invention also provides a pharmaceutical composition comprising am least one leustroducsin or a salt thereof in admixture with a pharmaceutically acceptable carrier or diluent.

The invention still further provides a method for the treatment or prophylaxis of: adverse reactions resulting from cancer chemotherapy or radiotherapy; infections; cancer; cerebral dysfunction; and fungal infections, which method comprises administering an effective amount of at least one leustroducsin or a salt thereof to a mammal, which may be human, suffering from or susceptible to such reactions, infections, cancer or dysfunction.

DETAILED DESCRIPTION OF INVENTION

The three leustroducsins of the present invention are as follows:

Leustroducsin A:

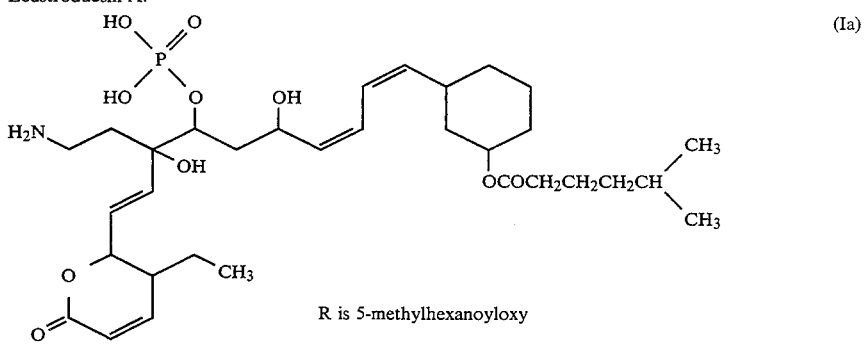

(Ia)

R is 5-methylhexanoyloxy

Leustroducsin B:

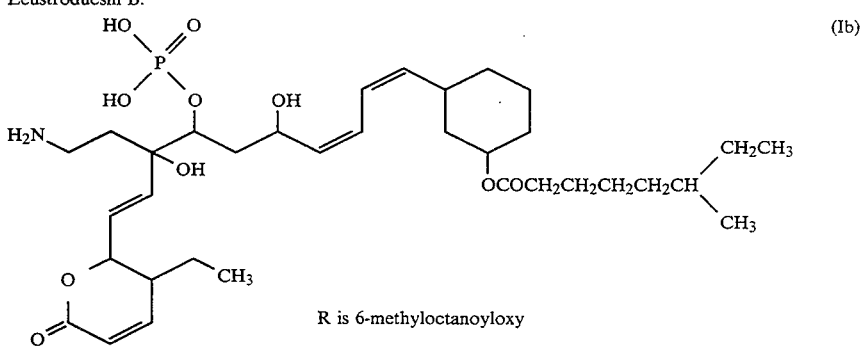

(Ib)

R is 6-methyloctanoyloxy

Leustroducsin C:

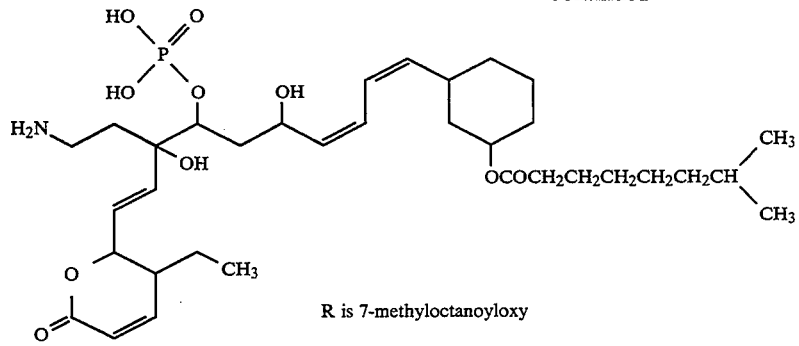

R is 7-methyloctanoyloxy

It is clear from the above formulae that the leustroducsins of the present invention contain a number of assymetric carbon atoms and several double bonds. They can therefore form various optical and geometric isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques. The leustroducsins of the present invention may be prepared by culturing a leustroducsin-producing microorganism of the genus Streptomyces, and then collecting one or more of the leustroducsins from the culture medium.

In particular, we especially prefer to employ as the microorganism a newly isolated strain of the genus Streptomyces, which we have established belongs to the species Streptomyces platensis and to which we have assigned the designation SANK 60191 (FERM BP-3288).

This microorganism was deposited under the terms of the Budapest Treaty at the Fermentation Research Institute, Agency of Industrial Science and Technology, on 20th February 1991 with the accession no. FERM BP-3288.

Details of the microbiological properties of Streptomyces platensis SANK 60191 (FERM BP-3288) are shown below.

1. Morphological characteristics

Streptomyces platensis SANK 60191 was cultured for 14 days at 28° C. on each of the agar media defined by the ISP (International Streptomyces Project). On microscopic observation after culture for 14 days, it was found that the substrate mycelium of this strain elongated and branched well and was colored yellowish gray or pale yellowish orange. However, neither the fragmentation nor the zig-zag elongation observable in Nocardioform actinomycetes were observed. Branching of the aerial mycelium was simple. The spore chains were a loose spiral in shape, and 10 to 50 or more spores formed a chain. Observation with a scanning electromicroscope showed the surface structure of the spores to be smooth. Spores were ovoid or oval, and 0.5–0.6×0.6–1.3 μm in size. Whirl of aerial mycelium, sclerotium, fragmentation of hyphae and specific organs, such as sporangia, could not be found.

2. Properties on various kinds of culture media

Table 1 shows the properties of the microorganism after culture for 14 days at 28° C. on various kinds of culture media. The colors are indicated by the color tip number given in the "Guide to Color Standard" edited by Nippon Shikisai Kenkyusho. This strain moistens and its color changes to black with the passage of time.

In the Table, the following abbreviations are used:
G: Growth; AM: Aerial mycelium; R: Reverse; SP: Soluble pigment; SC: Specific character

TABLE 1

| Medium | Item | Property of SANK 60191 |
|---|---|---|
| Sucrose-nitrate agar | G: | Good, smooth, pale yellowish orange (2-9-9) |
| | AM: | Good, velvety, light brownish gray (2-7-8) |
| | R: | Pale brown (2-8-9) |
| | SP: | No formation |
| Glucose-asparagine agar | G: | Good, smooth, pale yellowish orange (2-9-9) |
| | AM: | Moderate, velvety, white |
| | R: | Pale brown (2-8-9) |
| | SP: | No formation |
| Glycerol-asparagine agar (ISP 5) | G: | Very good, smooth, pale yellowish orange (2-9-9) |
| | AM: | Moderate, velvety, brownish gray (2-6-8) |
| | R: | Pale yellowish light brown (4-8-9) |
| | SP: | No formation |
| Inorganic salts-starch agar (ISP 4) | G: | Good, smooth, pale yellowish orange (2-9-9) |
| | AM: | Good, velvety, brownish white (1-6-6) |
| | R: | Brownish gray (2-5-9) |
| | SP: | No formation |
| | SC: | Aereal hyphae moisten and their color changes to black |
| Tyrosine agar (ISP 7) | G: | Very good, smooth, pale yellowish orange (2-9-9) |
| | AM: | Good, velvety, white, light brownish gray (2-7-8) spots |
| | R: | Pale yellowish brown (4-8-9) |
| | SP: | No formation |
| Nutrient agar (DIFCO) | G: | Good, smooth, pale yellowish orange (2-9-9) |
| | AM: | Moderate, velvety, white |
| | R: | Pale yellowish brown (4-8-9) |
| | SP: | No formation |
| Yeast extract-malt extract agar (ISP 2) | G: | Very good, smooth, pale yellowish orange (2-9-9) |
| | AM: | Abundant formation, velvety, light brownish white (1-7-6) |
| | R: | Pale yellowish brown (6-7-9) |
| | SP: | No formation |
| | SC: | Aerial hyphae moisten and their color changes to black |
| Oatmeal agar (ISP 3) | G: | Good, smooth, pale yellowish orange (2-9-9) |
| | AM: | Good, velvety, dark brownish gray (1-4-6) |
| | R: | Yellowish brown (4-6-9) |
| | SP: | No formation |
| Water agar | G: | Moderate, smooth, yellowish gray (1-9-10) |
| | AM: | Moderate, velvety, brownish gray |

TABLE 1-continued

| Medium | Item | Property of SANK 60191 |
| --- | --- | --- |
| | | (2-5-8) |
| | R: | Light brownish gray (2-7-8) |
| | SP: | No formation |
| Potato extract-carrot extract agar | G: | Moderate, smooth, yellowish gray (1-9-10) |
| | AM: | Moderate, velvety, brownish gray (2-5-8) |
| | R: | Light brownish gray (2-7-8) |
| | SP: | No formation |

3. Physiological properties

The physiological properties of strain SANK 60191 observed over the period of from day 2 to day 21 after the beginning of cultivation at 28° C. are shown in Table 2.

TABLE 2

| | |
| --- | --- |
| Hydrolysis of starch | Positive |
| Liquefaction of gelatin | Negative |
| Reduction of nitrates | Negative |
| Coagulation of milk | Negative |
| Peptonization of milk | Negative |
| Production of melanoid pigment | |
| (Medium 1)* | Negative |
| (Medium 2) | Negative |
| (Medium 3) | Negative |
| Decomposition of substrate | |
| Casein | Negative |
| Tyrosine | Positive |
| Xanthine | Positive |
| Temperature range for growth (Medium 4) | 9–35° C. |
| Optimum temperature for growth (Medium 4) | 20–26° C. |
| Sodium chloride tolerance | 10% |

*: Medium 1; Tryptone-yeast extract broth (ISP 1)
2; Peptone-yeast extract iron agar (ISP 6)
3; Tyrosine agar (ISP 7)
4; Yeast extract-malt extract agar (ISP 2)

Strain SANK 60191 was also cultivated at 28° C. using Pridham-Gottlieb agar (ISP 9) as the cultivation medium. The ultilization pattern of carbon sources observed after cultivation for 14 days is shown in Table 3.

TABLE 3

| D-Glucose | + | D-Fructose | + |
| --- | --- | --- | --- |
| L-Arabinose | – | L-Rhamnose | – |
| D-Xylose | – | Sucrose | + |
| Inositol | + | Raffinose | + |
| D-Mannitol | + | Control | – |

+ Utilization positive;
– Utilization negative.

4. Cellular Components

The cell walls of strain SANK 60191 were analyzed by the method of B. Becker et al. [Applied Microbiology, 12, 421–423 (1984)]. Since LL-diaminopimelic acid was detected, the cell walls was confirmed to be of Type I. Furthermore, the whole cell sugar components of strain SANK 60191 were analyzed by the method of M.P. Lechevalier [Journal of Laboratory & Clinical Medicine, 71, 934 (1968)]. No particular pattern was observed.

From these microbiological properties, this strain was confirmed to belong to the genus Streptomyces of the Actinomycetes. In comparison with the strains described in the ISP by E. B. Shirling and D. Gottlieb [International Journal of Systematic Bacteriology 18, 68–189 (1968); 18, 279–392 (1968); 19, 391–512 (1969); 22, 265–394 (1972)], and the strains described in other literature, such as "The Actinomycetes, Vol. 2" by S. A. Waksman, "Bergey's Manual of Determinative Bacteriology, 8th Edition (1974)" edited by R. E. Buchanan and N. E. Gibbons, "Bergey's Manual of Systematic Bacteriology, Vol. 4 (1989)", and in other recent literature about the Actinomycetes, this strain was considered to be very close to Streptomyces plantensis.

Furthermore, after liquid culture using a yeast-dextrose medium, strain SANK 60191 produced a soluble pigment having a fresh reddish brown color. On the addition of 0.05N aqueous hydrochloric acid, its color turned yellow, and, on the addition of 0.05N aqueous sodium hydroxide, no change was observed.

Streptomyces platensis produces a reddish or yellowish pigment after culture on yeast extract - malt extract agar, oatmeal agar, inorganic salts - starch agar, and glycerol - asparagine agar media. On the other hand, strain SANK 60191 hardly produced any of these pigments, which indicates a difference between this strain and the known strains of Streptomyces platensis. Since, however, the new strain and the known strains could only be distinguished by differences in the production of soluble pigments, SANK 60191 was identified as a new strain of Streptomyces platensis.

It has been established that strain SANK 60191 produces the leustroducsins. However, as is well known, the properties of fungi in general, and actinomycetous microorganisms in particular, can vary considerably and such fungi can readily undergo mutation, both through natural causes and as the result of induction by artificial means (for example, ultraviolet irradiation, radioactive irradiation, chemical treatment, etc.). Accordingly, the present invention embraces the use of any microorganism which can be classified within the genus Streptomyces and which shares with strain SANK 60191 the characteristic ability to produce the leustroducsins. The new microorganism, strain SANK 60191, is not expected to be exceptional, and the term "SANK 60191" thus is used to include all mutants of this strain which share with strain SANK 60191 the characteristic ability to produce the leustroducsins. Moreover, these mutants include those obtained by means of genetic engineering techniques, for example, recombination, transduction, transformation or the like. It is a matter of simple experimentation to determine, on the basis of the information given herein regarding the properties of the leustroducsins, whether any given strain produces these compounds or produces them in sufficient quantity to render that strain of potential commercial interest.

In addition to the new strain of Streptomyces platensis described above, we have also found that a known strain, namely Streptomyces platensis SAM-0654 (deposited at the Fermentation Research Institute, Japan under the accession number FERM BP-1668 on Jan. 22, 1988) also produces the leustroducsins of the present invention. This known strain is fully described in European Patent No. 329 361, the disclosure of which is incorporated herein by reference.

The leustroducsins of the present invention may be prepared by the culture of these strains of fungus in culture media of the type conventionally used for the production of other fermentation products from similar microorganisms. Such media necessarily contain microbiologically assimilable sources of carbon and of nitrogen as well as inorganic salts, as is well known to those skilled in the art.

Preferred examples of carbon sources include: glucose, fructose, maltose, sucrose, mannitol, glycerol, dextrin, oats, rye, corn starch, potato starch, corn flour, soybean meal, cottonseed cake, cottonseed oil, molasses, citric acid, tartaric acid and the like. Such compounds can be used alone or in any suitable combination. In general the amount used may vary in the range of from 1 to 10% by weight of the culture medium.

Preferred nitrogen sources are normally protein containing materials such as are commonly used in a fermentation process. Examples of such nitrogen sources include: soybean meal, wheat bran, peanut meal, cottonseed cake, cottonseed oil, cottonseed meal, casein hydrolyzates, fermamine, fish meal, corn steep liquor, peptone, meat extract, yeast, yeast extract, malt extract, sodium nitrate, ammonium nitrate, ammonium sulfate and the like. These nitrogen sources may be used alone or in any suitable combination. In general, we prefer to employ them at a concentration between 0.2 and 6% by weight of the culture medium.

The nutritive inorganic salts that may be incorporated into the culture medium are conventional salts that are capable of providing various ions necessary to the growth of microorganisms, such as sodium, ammonium, calcium, phosphate, sulfate, chloride and carbonate ions. In addition, the medium should contain minor amounts of essential trace elements, such as potassium, calcium, cobalt, manganese, iron and magnesium.

When the process of the present invention is carried out by a liquid culture technique, an antifoaming agent, such as a silicone oil, vegetable oil or surface-active agent, is preferably used in the culture medium. The pH of the culture medium for producing the leustroducsins by the cultivation of microorganisms of the genus Streptomyces, especially strain SANK 60191, preferably varies within the range of from 5.0 to 8.0, more preferably from 5.0 to 7.0.

The cultivation may be carried out at any temperature within the range of from 9° C. to 37° C. However, growth proceeds well at a temperature within the range of from 20° to 35° C. and such a temperature is preferred. A temperature of from 22° to 30° C. is preferred in order to optimise the production of the leustroducsins.

These compounds are produced under aerobic culture conditions and conventional aerobic culture methods, such as solid culture, shaking culture and aeration-stirring (submerged) culture methods, may be used. In the case of small scale cultivation, shaking culture for a few days at 28° C. is typically employed. In such a small scale culture method, the culture may be initiated with 1 or 2 proliferation steps, producing seed cultures in, for example, Erlenmeyer flasks, fitted with baffle plates, which serve as a liquid flow regulator. The medium for the seed culture steps preferably contains both carbon and nitrogen sources. In the preferred sequence of operations for such small scale cultivation, the seed culture flasks are shaken in a constant temperature incubator at 28° C. for 3 days or until sufficient growth is achieved. The grown seed culture is then transferred to a second seed medium or to the production medium. When an intermediate growth phase is used, essentially the same method is used for growth and an aliquot of the resulting intermediate product is inoculated into the production medium. The inoculated flask may be incubated for several days whilst shaking, and, after completion of the incubation, the contents of the flask may be centrifuged or filtered.

In the case of large scale production, the use of an appropriate fermentor equipped with a stirrer and an aeration apparatus is preferred. In this case, the nutritive medium can be prepared inside the fermentor. The medium is preferably sterilized by elevating the temperature to a suitable temperature, for example from 120° C. to 125° C.; after cooling, the sterilized medium my be inoculated with the previously prepared seed culture. The culture then proceeds under stirring and aeration at a suitable temperature, for example 28° C. This method is suitable for obtaining the compounds of the present invention in a large amount.

The change in the amount of leustroducsins produced with the passage of the culture time can be monitored by any suitable means, such as are well known in the fermentation art, for example high performance liquid chromatography. Most commonly, the amount of leustroducsins produced reaches a maximum after culturing for a period of from 48 hours to 96 hours.

After completion of the culture, the leustroducsins remaining in the liquid part of the medium liquid and in the bacterial cells can be extracted and purified by conventional means, making use of the physicohemical properties of the leustroducsins. For example, the leustroducsins present in the filtrate or in the supernatant can be extracted with a water-immiscible organic solvent, such as ethyl acetate, chloroform, ethylene chloride, methylene chloride or butanol (or with a mixture of any two or more of these solvents) under acidic conditions; after this it may be purified by conventional means. It is also possible to remove any impurities by extraction with one or more of the aforementioned solvents under basic conditions, after which it may be purified by conventional means. Alternatively, impurities can be removed by adsorption by passing a liquid containing the leustroducsins through a layer of a suitable adsorbent, or the leustroducsins can be adsorbed on a suitable adsorbent and then eluted using an appropriate eluent, such as aqueous methanol, aqueous acetone or aqueous butanol. Examples of suitable adsorbent s which may be used in these procedures include active carbon and adsorbent resins, such as Amberlite XAD-4 (a trade name for a product of Rohm & Haas) or Diaion HP-10, HP-20, CHP-20, HP-50 (trade names for products of Mitsubishi Chemical Industries Co.). Leustroducsins which are present in the cells can be obtained by extraction with a suitable solvent, such as 50–90% by volume aqueous acetone or aqueous methanol, followed by removal of the organic solvent; after this, the product can be subjected to similar extraction and purification procedures to those described above for the filtrate.

The leustroducsins thus obtained can be further purified by well known techniques, for example: adsorption column chromatography using a carrier, such as silica gel or magnesium-silica gel, for example that sold under the trade name "Florisil"; partition column chromatography using an adsorbent such as Sephadex LH-20 (a "trade name for a product of Pharmacia); or high performance liquid chromatography using a normal phase or reverse phase column. As is well known in the art, these isolation and purification procedures may be carried out alone or in any suitable combination, and, if desired, repeatedly, to isolate and purify the desired leustroducsins.

The leustroducsins of the present invention are novel compounds not previously reported in the literature. They stimulate the production of hematopoietic factors, such as G-CSF and GM-CSF, in animals (such as humans, dogs, cats and rabbits), and are, therefore, useful as therapeutic agents for reducing the side effects caused by cancer chemotherapy and radiotherapy; they also prevent infections and exhibit an anticancer effect through the activation of macrophages. In addition, the leustroducsins are expected to be useful for improving cerebral metabolism by stimulating the production of NGF. Furthermore, they are useful as antifungal agents and have demonstrated an antifungal effect against *Tricophyton metagrophytes.*

The ability of the leustroducsins to stimulate the production of hematopoietic factors in accordance with the present invention can, in principle, be assayed by the method by Kohama et al. [Experimental Hematology 16, 603–608 (1988)]. In this method, a production system for various hematopoietic factors and an assay system for Various hematopoietic factors are combined. KM-102 cells, for example, which originated from human bone marrow stromal cells, may be employed to produce various hematopoietic factors. However, any cells capable of the production of various hematopoietic factors may be used instead, for example primary cultured bone marrow stromal cells, vascular endothelial cells, lymphocytes, or macrophages which exist in the bone marrow. A test sample of the compound whose activity is to be assessed is diluted to a suitable concentration and added the culture system containing the cells which produce various hematopoietic factors ("HF-producing cells"). After a suitable period, usually 24 hours, a part of the supernatant of the culture medium is taken, and added to a culture system of cells which are dependent on various hemalopoietic factors, for example, TF-1 cells and NFS-60 cells, ("HF-dependent cells") at a suitable concontradict. After a certain time, the amount of hematopoietic factors can be measured by measuring the growth of the HF-dependent cells, and thus the ability of the compound to stimulate the production of various hematopoietic factors can be assayed. The growth of the HF-dependent cells may be determined by any conventional method, such as the incorporation of tritium-thymidine by the cells or using an MTT [3-(4,5-dimethylthiazol-2-yl)-2,5-diphenyltetrazolium bromide] assay method (Chemicon International Inc., USA). The assay of various hematopoietic factors may be carried out by any conventional method, such as the colony-forming method or the ELISA method.

The leustroducsins of the present invention contain both an acidic group (the phosphoric acid group) and a basic group (the amino group) and can thus form salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. The compounds of the present invention can form salts with bases. Examples of such salts include: salts with an alkali metal, such as sodium, potassium or lithium; salts with an alkaline earth metal, such as barium or calcium; salts with another metal, such as magnesium or aluminum; organic base salts, such as a salt with dicyclohexylamine; and salts with a basic amino acid, such as lysine or arginine. The compounds of the present invention can also form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspattic acid.

When these compounds are intended for therapeutic use, they may be administered alone or in a suitable pharmaceutical formulation containing, in addition to the active compound, one or more conventional diluents, carriers, excipients or adjuvants. The nature of the formulation will, of course, depend on the intended route of administration. However, for the oral route, the compound is preferably formulated as powders, granules, tablets, capsules or syrups. For parentoral administration, it is preferably formulated as an injection (which may be intravenous, intramuscular or subcutaneous) or as drops or suppositories. These preparations can be prepared by known means by adding such additives as vehicles, binders, disintegrators, lubricants, stabilizers, corrigents, solubilizing agents, suspending agents or coating agents. Although the dosage may vary depending upon the symptoms and age. of the patient, the nature and severity of the disease or disorder and the route and manner of administration, in the case of oral administration to an adult human patient, the compounds of the present invention may normally be administered at a daily dose of from 1 mg to 1000 mg. The compounds may be administered in a single dose, or in divided doses, for example two or three times a day.

The preparation of the compounds of the present invention is further illustrated by the following non-limiting Examples.

EXAMPLE 1

Culture and isolation of leustroducsins

1(A) Culture

One platinum loopful of spores of *Streptomyces platensis* SANK 60191 was inoculated into a 500 ml Erlenmeyer flask fitted with baffle plates and containing 100 ml of a previously sterilized culture medium (having the composition described below), and the microorganism was cultured for 3 days at 28° C. and at 200 rpm (a rotation radius of 7 cm), using a rotary shaker.

| Culture Medium: | |
| --- | --- |
| Soluble starch | 30 g |
| Raw yeast | 10 g |
| Soy bean powder | 7 g |
| Fish meal | 5 g |
| Corn steep liquor | 2 g |
| Meat extract | 1 g |
| Calcium carbonate | 1 g |
| Water to | 1000 ml |
| | pH 7 (before sterilization). |

15 liters of the same culture medium as was used for the seed culture was charged into each of four 30 liter stainless jal fermenters, and was sterilized by heating it at 120° C. for 30 minutes. 150 ml of the seed culture liquid prepared as described above were then added. The mixture was cultivated for 3 days am 28° C. with aeration at an air flow rate of 15 liters/minute, whilst stirring. In order for the oxygen concentration in the liquid to be maintained at 5 ppm, the stirring rate was automatically controlled within the range from 100 to 300 rpm.

1(B) Isolation 2.4 kg of Celite 545 (a trade name for a product of Johns & Manville Project Corporation, USA) were added as a filter aid to 60 liters of the culture liquid obtained as described in 1(A) above, and the mixture was filtered. After filtration of the culture liquid, 7.2 kg of bacterial cells were obtained. The cells were extracted once with 30 liters of 50% v/v aqueous acetone, and twice with 20 liters of 80% v/v aqueous acetone each time. These extracts were combined and the organic solvent was distilled off using a rotary evaporator. Sufficient aqueous hydrochloric acid was added to the residue to adjust its pH to a value of 2.0, and then the mixture was extracted twice, each time with 10 liters of ethyl acetate. The extracts were combined, and 10 liters of a 1% w/v aqueous solution of sodium hydrogencarbonate were added to the combined extracts. The active fractions were transferred into the aqueous layer and the ethyl acetate layer was removed. This ethyl acetate layer was again extracted with 5 liters of a 1% w/v aqueous solution of sodium hydrogencarbonate. The sodium-hydrogencarbonate solutions were combined and the pH of the combined solution was adjusted to a value of 2.0 by the addition of aqueous hydrochloric acid. The solution was extracted twice, each time with 10 liters of ethyl acetate. The organic extracts were combined, washed with water and then with a saturated aqueous solution of sodium chloride, and then dried over anhydrous sodium sulfate. During continuous addition of methanol, the solution was then condensed by evaporation under reduced pressure, using a rotary evaporator, obtain 10 ml of an oily substance. This oily substance was dissolved in 100 ml of 60% v/v aqueous methanol, and the resulting solution was adsorbed on Sep-Pak Vac 20 cc $C_{18}$ Cartridges (a trade name for a product of Waters Col., USA). Impurities were eluted with 30 ml of 60% v/v aqueous methanol. The leustroducsins were then eluted with 15 ml of 100% methanol, and the eluate was condensed to obtain 800 mg of an oily substance. This oily substance was dissolved in 10 ml of methanol, and subjected to high performance liquid chromatography. The fractions showing peaks near 13 minutes and 24 minutes were collected and are referred to as "Raw Fraction A" and "Raw Fraction B", respectively. The conditions used for the chromatography are shown below.

Preparative liquid chromatography
Column: Radial-Pak 25×10 (Waters, USA)
Eluting solvent: 50% by volume aqueous acetonitrile, containing 0.5% triethylamine - phosphate buffer, pH 3.0
Flow rate: 9 ml/min.
Wave length: 230 nm After condensation of all of these peaks, the resulting fractions were subjected to preparative high performance liquid chromatography. Raw Fraction A was subjected to preparative chromatography to collect the peak near 56 minutes under the following conditions; it was then desalted and condensed using Sep-Pak to obtain 11.66 mg of leustroducsin A.

Preparative conditions for Raw Fraction A
Column: Cosmosil 5C 18-AR 20×250 mm (Nakaraitesque Inc.)
Eluting solvent: 42% v/v aqueous acetonitrile, containing 0.5% triethylamine phosphate buffer, pH 3.0
Flow rate: 9 ml/min.
Wave length: 230 nm.

Raw Fraction B was subjected to preparative chromatography to collect the peaks near 47 and 51 minutes under the following conditions; it was then desalted and condensed using Sep-Pak to obtain 9.83 mg of leustroducsin B and 5.22 mg of leustroducsin C.

Preparative conditions for Raw Fraction B
Column: Cosmosil 5C 18-AR 20×250 mm (Nakaraitesque Inc.)
Eluting solvent: 47% v/v aqueous acetonitrile, containing 0.5% triethylamine - phosphate buffer, pH 3.0
Flow rate: 9 ml/min.
Wave length: 230 nm.

The leustroducsins thus obtained had the following properties:

Leustroducsin A:

1) Chemical structure: formula (Ia), shown above.
2) Nature: Acidic and fat soluble.
3) Color: Pale yellow oil.
4) Molecular formula: $C_{32}H_{52}O_{10}NP$.
5) Molecular weight: 641, determined by the FAB-MS method ("FAB-MS" is Fast Atom Bombardment Mass Spectrometry).
6) Ultraviolet absorption spectrum: 234 nm <maximum absorption in methanol).
7) Infrared absorption spectrum: the infrared spectrum showed the following absorption maxima (liquid film, $\nu_{max}cm^{-1}$): 2933, 2867, 1728, 1464, 1383, 1248, 1176, 1056, 969.
8) $^1$H-Nuclear magnetic resonance spectrum: the Nuclear magnetic resonance spectrum (270 MHz) in heavy methanol, using trimethylsilane as the internal standard, is shown below:

7.08 (1H, doublet of doublets, J=9.8 & 4.9 Hz);
6.21–6.35 (2H, multiplier);
6.06 (1H, doublet of doublets, J=15.6 & 6.1 Hz);
6.02 (1H, doublet of doublets, J=9.8 & 1.4 Hz);
5.94 (1H, doublet, J=15.6 Hz);
5.46 (1H, multiplier);
5.31 (1H, multiplier);
5.10 (1H, doublet of doublets, J=6.1 & 4.4 Hz);
4.94 (1H, multiplier);
4.72 (1H, multiplier);
4.29 (1H, triplet of doublets, J=10.1, 10.1 & 2.4 Hz);
2.93–3.15 (2H, multiplier);
2.50–2.71 (2H, multiplier);
2.25 (2H, triplet, J=7.6 Hz);
2.16 (1H, multiplier);
0.99–2.01 (18H, multiple);
0..95 (3H, triplet, J=7.6 Hz);
0.89 (6H, doublet, J=6.8 Hz).

1) $^{13}$C-Nuclear magnetic resonance spectrum: (δ: ppm): the Nuclear magnetic resonance spectrum (270 MHz) in heavy methanol, using trimethylsilane as the internal standard, is shown below:

11.4 (quartet), 22.7 (triplet), 22.9 (quartet),
22.9 (quartet), 24.0 (triplet), 24.7 (triplet),
28.9 (doublet), 32.4 (triplet), 33.1 (triplet),
34.3 (triplet), 35.7 (triplet), 36.1 (doublet),
37.1 (triplet), 39.4 (triplet), 39.5 (triplet),
40.6 (doublet), 40.6 (triplet), 64.7 (doublet),
73.9 (doublet), 77.8 (singlet), 78.5 (doublet),
82.3 (doublet), 121.1 (doublet), 123.7 (doublet),
124.3 (doublet), 127.7 (doublet), 135.3 (doublet), 137.3 (doublet), 138.2 (doublet), 152.7 (doublet), 166.3 (singlet), 175.0 (singlet).

10) Solubility:

Soluble in alcohols, such as methanol, ethanol or butanol; and soluble in acetone, chloroform, ethyl acetate and dimethyl sulfoxide; limited solubility in water; insoluble in hexane.

11) Color reactions:

Positive to sulfuric acid, iodine, nonhydrin and ammonium molybdate-perchloric acid reactions.

12) High performance liquid chromatography:

Separating column: Cosmosil 5C18-AR (Column size, 4.6×250 mm, Product of Nakaraitesgue Inc.)
Solvent: 45% v/v aqueous acetonitrile, containing 0.5% triethylamine - phosphate buffer (pH 3)
Flow rate: 1 ml/min.
Wave length: 230 nm
Retention time: 9.06 min. and 9.16 min.

Leustroducsin B:

1) Chemical structure: formula (Ib), shown above.
2) Nature: Acidic and fat soluble.
3) Color: Pale yellow oil.
4) Molecular formula: $C_{34}H_{56}O_{10}NP$.
5) Molecular weight: 669, determined by the FAB-MS method.
6) Ultraviolet absorption spectrum: 234 nm (maximum absorption in methanol).
7) Infrared absorption spectrum: the infrared spectrum showed the following absorption maxima (liquid film, $\nu_{max}cm^{-1}$): 2927, 2855, 1729, 1463, 1380, 1250, 1172, 1056, 968.
8) $^1$H-Nuclear magnetic resonance spectrum: the Nuclear magnetic resonance spectrum (270 MHz) in heavy methanol, using trimethylsilane as the internal standard, is shown below:

7.09 (1H, doublet of doublets, J=9.8 & 4.9 Hz);
6.21-6.35 (2H, multiplier);
6.07 (1H, doublet of doublets, J=15.6 & 6.1 Hz);
6.02 (1H, doublet of doublets, J=9.8 & 1.5 Hz);
5.94 (1H, doublet, J=15.6 Hz);
5.46 (1H, multiplier);
5.31 (1H, multiplier);
5.10 (1H, doublet of doublets, J=6.1 & 4.4 Hz);
4.94 (1H, multiplet);
4.72 (1H, multiplet);
4.29 (1H, triplet of doublets, J=9.9, 9.9 & 2.6 Hz);
2.93-3.15 (2H, multiplet);
2.50-2.71 (2H, multiplet);
2.27 (2H, triplet, J=7.3 Hz);
2.17 (1H, multiplet);
1.00-2.01 (22H, multiplet);
0.95 (3H, triplet, J=7.5 Hz);
0.87 (3H, triplet, J=6.8 Hz);
0.86 (3H, doublet, J=6.6 Hz).

9) $^{13}$C-Nuclear magnetic resonance spectrum: (δ: ppm): the Nuclear magnetic resonance spectrum (270 MHz) in heavy methanol, using trimethylsilane as the internal standard, is shown below:

11.4 (quartet), 11.7 (quartet), 19.6 (quartet), 22.7 (triplet), 24.7 (triplet), 26.4 (triplet), 27.6 (triplet), 30.6 (triplet), 32.4 (triplet), 33.1 (triplet), 34.1 (triplet), 35.5 (triplet), 35.5 (doublet), 36.1 (doublet), 37.1 (triplet), 37.3 (triplet), 39.4 (triplet), 40.6 (doublet), 40.6 (triplet), 64.7 (doublet), 73.9 (doublet), 77.8 (singlet), 78.5 (doublet), 82.3 (doublet), 121.0 (doublet ), 123.7 (doublet), 124.3 (doublet), 127 .7 (doublet), 135.2 (doublet), 137.4 (doublet ), 138.2 (doublet), 152.7 (doublet), 166 .4 (singlet), 175.1 (singlet).

10) Solubility:

Soluble in alcohols, such as methanol, ethanol or butanol; and soluble in acetone, chloroform, ethyl acetate and dimethyl sulfoxide; limited solubility in water; insoluble in hexane.

11) Color reactions:

Positive to sulfuric acid, iodine, nonhydrin and ammonium molybdate-perchloric acid reactions.

12) High performance liquid chromatography:

Separating column: Cosmosil 5C18-AR (Column size, 4.6×250 mm, Product of Nakaraitesgue Inc.)
Solvent: 45% v/v aqueous acetonitrile, containing 0.5% triethylamine - phosphate buffer (pH 3)
Flow rate: 1 ml/min.
Wave length: 230 run
Retention time: 20.62 min. and 20.87 min.

Leustroducsin C:

1) Chemical structure: formula (Ic), shown above.
2) Nature: Acidic and fat soluble.
3) Color: Pale yellow oil.
4) Molecular formula: $C_{34}H_{56}O_{10}NP$.
5) Molecular weight: 669, determined by the FAB-MS method.
6) Ultraviolet absorption spect-rum: 234 run (maximum absorption in methanol).
7) Infrared absorption spectrum: the infrared spectrum showed the following absorption maxima (liquid film, $\nu_{max}cm^{-1}$):
2930, 2856, 1728, 1464, 1382, 1252, 1172, 1056, 968.
8) $^1$H-Nuclear magnetic resonance spectrum: the Nuclear magnetic resonance spectrum (270 MHz) in heavy methanol, using trimethylsilane as the internal standard, is shown below:

7.08 (1H, doublet of doublets, J=9.8 & 4.9 Hz);
6.21-6.35 (2H, multiplet);
6.07 (1H, doublet of doublets, J=15.6 & 6.1 Hz);
6.02 (1H, doublet of doublets, J=9.8 & 1.5 Hz);
5.94 (1H, doublet, J=15.6 Hz);
5.46 (1H, multiplet);
5.31 (1H, multiplet);
5.10 (1H, doublet of doublets, J=6.1 & 4.9 Hz);
4.94 (1H, multiplet);
4.72 (1H, multiplet);
4.28 (1H, triplet of doublets, J=10.1, 10.1 & 2.4 Hz);
2.93-3.15 (2H, multiplet);
2.50-2.71 (2H, multiplet);
2.27 (2H, triplet, J=7.3 Hz );
2.16 (1H, multiplet);
1.00-2.01 (22H, multiplet);
0.95 {3H, triplet, J=7.3 Hz );
0.88 (6H, doublet, J=6.3 Hz).

9) $^{13}$C-Nuclear magnetic resonance spectrum: (δ: ppm): the Nuclear magnetic resonance spectrum (270 MHz) in heavy methanol, using trimethylsilane as the internal standard, is shown below:

11.4 (quartet), 22.7 (triplet), 23.1 (quartet), 23.1 (quartet), 24.7 (triplet), 26.2 (triplet), 28.2 (triplet), 29.1 (doublet), 30.4 (triplet), 32.4 (triplet), 33.1 (triplet), 34.2 (triplet), 35.4 (triplet), 36.1 (doublet), 37.1 (triplet), 39.4 (triplet), 40.0 (triplet), 40.6 (doublet), 40.6 (triplet), 64.6 (doublet), 73.9 (doublet), 77.8 (singlet), 78.4 (doublet), 82.3 (doublet), 121.1 (doublet), 123.7 (doublet), 124.3 (doublet), 127.7 (doublet), 135.2 (doublet), 137.3 (doublet), 138.2 (doublet), 152.7 (doublet), 166.4 (singlet), 175.0 (singlet).

10) Solubility:

Soluble in alcohols, such as methanol, ethanol or butanol; and soluble in acetone, chloroform, ethyl acetate and dimethyl sulfoxide; limited solubility in water: insoluble in hexane.

11) Color reactions:

Positive to sulfuric acid, iodine, nonhydrin and ammonium molybdate-perchloric acid reactions.

12) High performance liquid chromatography:

Separating column: Cosmosil 5C18-AR (Column size, 4.6×250 mm, Product of Nakaraitesque Inc.)
Solvent: 45% v/v aqueous acetonitrile, containing 0.5% triethylamine - phosphate buffer (pH 3)
Flow rate: 1 ml/min.
Wave length: 230 nm
Retention time: 21.90 min. and 22.19 min.

BIOLOGICAL ACTIVITY

The following Test Examples will explain the effect of the compounds of the present invention in more detail.

TEST EXAMPLE 1

Stimulation of GM-CSF production:

Determination of the stimulation of GM-CSF production by the compounds of the present invention was carried out, in principle, using a combination of the method of Kohama et al. [Experimental Hematology 603–608 (1988)] and that of Kitamura et al. [Journal of Cellular Physiology 140, 323–334 (1989)]. In more detail, KM-102 cells originating from human bone marrow stromal cells, which served as to produce GM-CSF, were mixed with a test sample solution diluted to a suitable concentration (the "GM-CSF producing system"). After incubation for 24 hours, a part of the culture supernatant was taken and was added to a culture system of GM-CSF-dependent human TF-1 cells. After between 48 and 72 hours, the amount of GM-CSF was measured by the growth of TF-1 cells (the "GM-CSF assay system") to obtain a measure of the stimulation of GM-CSF production. The growth of TF-1 cells was determined by tritium thymidine pulse-labelling for 4 hours. Similar results were obtained also by means of an MTT kit (Chemicon International Inc. USA) to assay the growth of TF-1 cells and by means of an ELISA kit (Genzyme Inc. USA) to assay the GM-CSF. Whether the GM-CSF production inducing system functioned normally or not was assayed by means of recombinant interleukin $1\beta$(IL-$1\beta$: Genzyme Inc. USA). IL-$1\beta$ induced GM-CSF production in a dose-dependent manner within the range from 1 to 100 units/ml, and, at a maximum, the production of GM-CSF induced was from 10 to 20 times the production without IL-$1\beta$, showing a normal functioning of the experimental system.

After each addition of leustroducsin A, B or C to the KM-102 cells at a certain concentration, GM-CSF production was found to be induced in a dose-dependent manner. At the maximum, the amount of GM-CSF produced was from 10 to 20 times the amount produced without the addition. The $ED_{50}$ values were found to be 180+50, 50+15 and 50+15 ng/ml for leustroducsins A, B and C respectively.

TEST EXAMPLE 2

Stimulation of G-CSF production:

Stimulation of G-CSF production was assayed by a system in which the GM-CSF assay system employed inTest Example 1 was replaced by a G-CSF assay system [as described by Shirafuji et al.: Experimental Hematology 17, 116–119 (1989)]. In more detail, KM-102 cells originating from human bone marrow stromal cells, which served to produce G-CSF, were added to a leustroducsin solution diluted to a suitable concentration (the "G-CSF producing system"). After incubation for 24 hours, a part of the culture supernatant was taken, and added to a culture system of G-CSF-dependent NFS-60 cells. After between 24 and 48 hours, the amount of G-CSF was assayed from the growth of NFS-60 cells (the "G-CSF assay system") to obtain a measure of the stimulation of G-CSF production. The growth of NFS-60 cells was determined by tritium-thymidine pulse-labelling for 4 hours. Similar results were also obtained by means of an MTT kit to assay the growth of NFS-60 cells and by means of an ELISA kit to assay the G-CSF [Motojima et al.: Journal of immunological Methods 118, 187–192 (1989)]. Whether the G-CSF production inducing system functioned normally or not was assayed by means of recombinant interleukin $1\beta$ (IL-$1\beta$: Genzyme Inc. USA). IL-$1\beta$ induced GM-CSF production in a dose-dependent fashion within a range from 1 to 100 units/ml, and at the maximum the production of G-CSF induced was from 10 to 20 times the production without IL-$1\beta$, showing normal functioning of the experimental system.

After each addition of leustroducsins A, B and C to KM-102 cells at a certain concentration, G-CSF production was found to be induced in a dose-dependent fashion. At the maximum, the amount of G-CSF produced was from 10 to 20 times the amount produced without the addition. The $ED_{50}$ values were found to be 200+50, 50+15 and 50+15 ng/ml for leustroducsins A, B and C respectively.

TEST EXAMPLE 3

Stimulation of NGF production

Furukawa et al. reported that fibroblast-forming L-M cells derived from mouse connective tissue produce and secrete a relatively large amount of NGF, and that catecolamines stimulate this production and secretion [J. Biol. Chem. 261, 6039–6047 (1986)]. We examined whether the leustroducsins stimulate NGF production and secretion or not.

L-M cells were cultivated using 199 medium containing 0.5% peptone. Into each well of a 24-well culture plate, $5 \times 10^4$ of L-M cells were inoculated, and cultured in a $CO_2$ incubator (37° C., 5% $CO_2$) until confluent. The culture liquid was removed, and the cells were washed once with 199 medium containing 0.5% bovine serum albumin (Sigma). One of the leustroducsins was added at a certain concentration to 199 medium containing 0.5% bovine serum albumin, and then the L-M cells were treated with this mixture. The L-M cells were then cultured in a $CO_2$ incubator for 24 hours. After collecting the culture liquid, the NGF in the liquid was assayed.

The NGF was assayed by enzyme immunoassay [Proc. Natl. Acad. Sci. USA 80, 3513–3516 (1983)]. Into each well of a polystyrene 96-well plate, 75 $\mu l$ of anti-mouse-$\beta$NGF antibody (Boehringer) solution (0.3 $\mu g/ml$, pH 9.6) was poured, and allowed to stand for 1 hour at room temperature. After removal of the antibody, all of the wells were washed with a wash solution three times. 50 $\mu l$ of the standard $\beta$NGF (Wako Pure Chem. Ind.) or of the standard solution was poured into each well, and the mixture was allowed to stand for from 6 to 8 hours at room temperature. At the end of this time, the standard μNGF or standard solution was removed, and all of the wells were washed three times. 50β1 of labelled anti-μNGF monoclonal antibody (Boehringer) solution (100 mU/ml, pH 7.0) was poured into each well, and the solution was allowed to stand for from 15 to 18 hours at 4° C. At the end of this time, the enzyme-labelled antibody was removed, and all of the wells were washed three times. 100 μl of chlorophenoi-μ-D-galactoside (Boehringer) solution (1 mg/ml, pH 7.3) was then poured into each well. After a proper color had developed (after 2 to 3 hours at room temperature), the absorbance at 570 nm was determined. The amount of NGF was calculated from the standard curve, and this was related as a percentage to the amount of NGF produced and secreted from the cells without leustroducsin treatment.

The leustroducsins were all found to stimulate the production of NGF in a dose-dependent fashion. At 5 μ/ml of each leustroducsin, 2 times or more NGF production was induced compared with that in the cells without treatment.

TEST EXAMPLE 4

Antifungal activity

In order to examine the antifungal activity of leustroducsins against fungi pathogenic to animals, the activity was tested against *Tricophyton mentagrophytes*. For each of leustroducsins, an inhibitory circle was observed at a concentration of 1 μg/disc.

TEST EXAMPLE 5

Acute toxicity

According to the conventional procedure, the acute toxicity was tested in five ddY mice (male). After intraperitoneal administration of a dose of 0.2 mg/kg of leustroducsin A, no toxicity was observed over a period of 5 days. Similarly, no toxicity was observed after administration of leustroducsin B, leustroducsin C and their related derivatives.

From the results reported above, it is apparent that leustroducsins, A, B and C stimulate the production of hematopoietic factors such as granulocyte colony-stimulating factor and granulocyte macrophage colony-stimulating factor. Accordingly, the leustroducsins are useful as therapeutic agents to reduce side effects caused by cancer chemotherapy and radiotherapy. They also protect against infection and have an anticancer effect through activation of macrophages. In addition, the leustroducsins are useful to improve cerebral metabolism by stimulating production of NGF. Furthermore, the leustroducsins are useful as antifungal agents as shown by their antifungal effect against *Tricophyton mentagrophytes*.

We claim:

1. A process for producing at least one leustroducsin of formula (I):

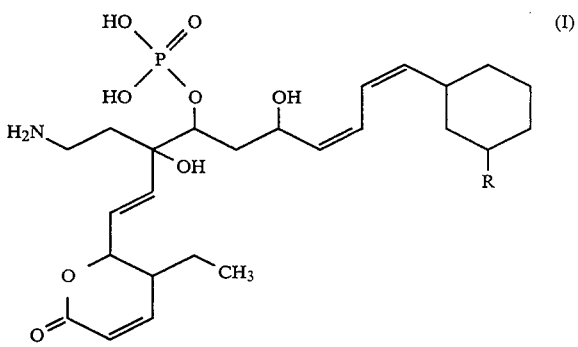

in which R represents a 5-methylhexanoyloxy group, a 6-methyloctanoyloxy group or a 7-methyloctanoyloxy group, or a pharmaceutically acceptable salt thereof, which comprises cultivating a microorganism strain of the genus *Strepmyces* and the species *platensis* which produces said at least one leustroducsin of said formula (I), separating from the resultant culture said at least one leustroducsin of said formula (I) and purifying said at least one leustroducsin of said formula (I).

2. The process of claim 1, in which said leusnroducsin has the formula (Ia):

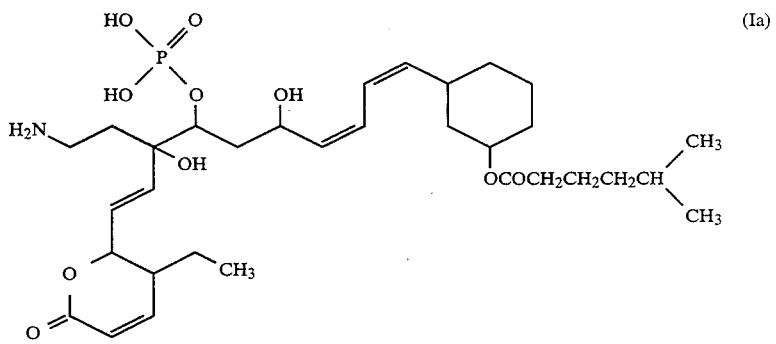

3. The process of claim 1, in which said leustroducsin has the formula (Ib):

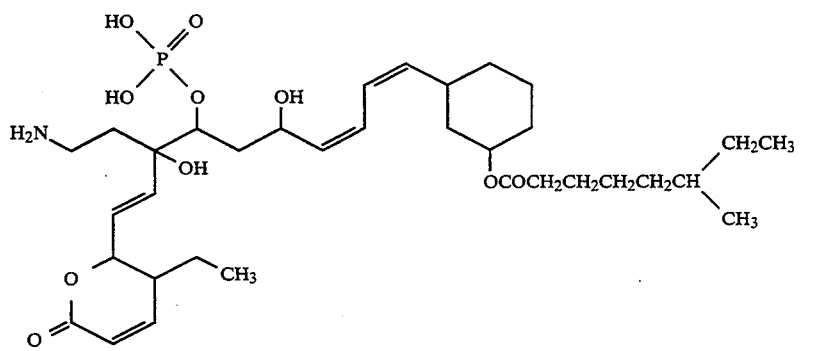

(Ib)

4. The process of claim 1, in which said leustroducsin has the formula (Ic):

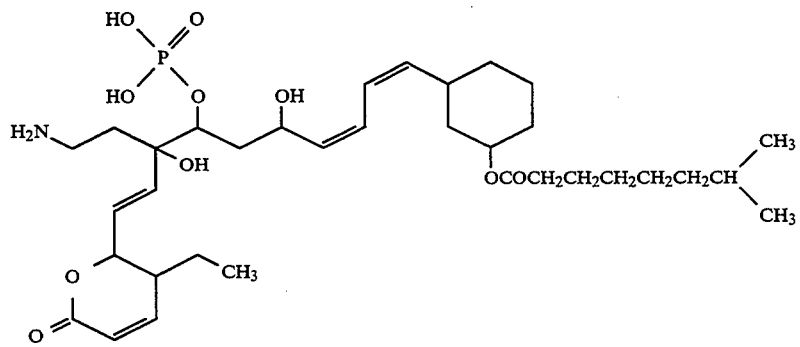

(Ic)

5. The process of claim 1, in which said microorganism is *Streptomyces platensis* SANK 60191 (FERM BP-3288).

6. The process of claim 1, wherein the cultivating is conducted at a pH of 5.0 to 8.0.

7. The process of claim 1, wherein the cultivating is conducted at a pH of 5.0 to 7.0.

8. The process of claim 7, wherein the cultivating is conducted at a temperature of 9° C. to 37° C.

9. The process of claim 7, wherein the cultivating is conducted at a temperature of 20° C. to 35° C.

10. The process of claim 7, wherein the cultivating is conducted at a temperature of 22° C. to 30° C.

* * * * *

UNITED STATES PATENT AND TRADEMARK OFFICE
CERTIFICATE OF CORRECTION

PATENT NO. : 5,443,972
DATED : August 22, 1995
INVENTOR(S) : KOHAMA et al

It is certified that error appears in the above-indentified patent and that said Letters Patent is hereby corrected as shown below:

Column 2, line 59: "The" should begin a new paragraph.

Column 2, line 60: delete "331" and insert --1331--.

Column 5, line 29: "The" should begin a new paragraph.

Column 14, line 55: delete "1)" and insert --9)--.

Signed and Sealed this

Ninth Day of April, 1996

Attest:

BRUCE LEHMAN

Attesting Officer    Commissioner of Patents and Trademarks